United States Patent [19]
Ruiz

[11] Patent Number: 5,928,261
[45] Date of Patent: Jul. 27, 1999

[54] REMOVABLE VASCULAR FILTER, CATHETER SYSTEM AND METHODS OF USE

[76] Inventor: Carlos E. Ruiz, 1747 N. Country La., Pasadena, Calif. 91107

[21] Appl. No.: 09/107,153

[22] Filed: Jun. 29, 1998

[51] Int. Cl.⁶ .................................................. A61B 17/00
[52] U.S. Cl. .......................................... 606/200; 606/159
[58] Field of Search .................................... 606/200, 159, 606/198, 199, 195, 194, 191; 604/22, 104; 623/1, 11, 12; 128/899

[56] References Cited

U.S. PATENT DOCUMENTS 4,723,549  2/1988  Wholey et al. ......................... 128/344
5,160,342  11/1992  Reger et al. ............................ 606/200

*Primary Examiner*—John J. Wilson
*Assistant Examiner*—Pedro Philogene
*Attorney, Agent, or Firm*—Fish & Neave; Nicola A. Pisano

[57] ABSTRACT

A removable vascular filter and apparatus and methods for removing the removable vascular filter are provided. The removable vascular filter is held in place by a coiled-sheet stent portion having a magnetic band disposed on its interior edge. A catheter system is also provided having an electromagnet configured to engage the magnetic band and enable the coiled-sheet stent portion and filter sack to be wound to a reduced diameter to facilitate transluminal removal of the vascular filter and its contents.

20 Claims, 3 Drawing Sheets

REMOVABLE VASCULAR FILTER, CATHETER SYSTEM AND METHODS OF USE

FIELD OF THE INVENTION

The present invention relates to apparatus and methods for filtering fluid flow within a vascular system, such as the bloodstream. More particularly, the present invention provides a removable filter for intraluminal use, and catheter apparatus and methods for percutaneous placement and removal of the filter.

BACKGROUND OF THE INVENTION

Commonly used minimally-invasive procedures for relieving stenoses, such as angioplasty or atherectomy, may dislodge plaque or blood clots. Once dislodged, such atheroma may be carried downstream by the blood and occlude smaller vessels, potentially cutting off the flow of blood to tissue. Such a blockage may present a serious risk to a patient's health, especially if the blockage occurs in a critical vessel leading to the heart or brain.

Moreover, procedures in which foreign objects are introduced into the bloodstream may cause the formation of clots. These clots, if released into the bloodstream, may also block the flow of blood, with potentially life-threatening consequences.

To reduce the risk of embolism, numerous previously known methods have been, and are being, developed. One previously known method, under development by Percusurge, Inc., Sunnyvale, Calif., involves temporarily blocking blood flow in an area in which a procedure is to be performed using a balloontipped occlusion catheter. Materials proximal of the blockage are evacuated from the vessel upon completion of the procedure, the occlusion catheter is removed, and the flow of blood is restored.

The foregoing method has serious drawbacks, however. For example, depending upon the vessel being occluded, the blood flow may only be blocked for a limited time before there is a risk of damage to tissue fed by the blocked vessel. Additionally, use of a balloon-tipped occlusion catheter to block flow may disrupt or loosen plaque within a vessel, much like an angioplasty balloon. This plaque may be released into the bloodstream after the balloon-tipped catheter is removed, possibly causing an embolism.

Another previously known method of reducing the risk of embolization uses a filter to catch loose plaque and clots, while permitting blood to pass through the filter. Numerous implantable filter devices have been developed to prevent clots from reaching critical areas, such as the heart or brain. These filter devices generally are removable only by surgery, especially if a filter device has remained in a vessel for an extended period, e.g., several weeks. Due to the difficulty with removing such devices, previously known filter devices generally are not appropriate for use with procedures such as angioplasty or atherectomy. Also, because these filter devices typically are constructed of a loose wire mesh, they filter out only large clots or plaque fragments.

For example, patients afflicted with chronic thrombophlebitis of the lower extremities often have recurrent pulmonary thromboembolism, which is treated by interruption of the vena cava with implantable filters. Because permanent obstruction of the vena cava can itself have detrimental effect on the patient's health, it would be desirable to provide implantable vascular filters that could be removed after a desired period of implantation.

Apart from implantable filter devices, a number of removable filter devices have been developed for short term use. These devices typically comprise a filter attached to a distal end of a device used during an angioplasty procedure. For example, U.S. Pat. No. 4,723,549, to Wholey et al. shows an angioplasty catheter having a filter disposed near its distal end; U.S. Pat. No. 5,160,342, to Reger et al. describes a guide wire having a filter disposed at its distal end. Such filter devices typically are kept in place only for the duration of a procedure, and are not appropriate for use over an extended period.

In view of the above, it would be desirable to provide a vascular filter device and catheter system that enable the vascular filter to be readily implanted and removed.

It would also be desirable to provide a vascular filter device that may be readily implanted within a vessel, remain in place for an extended period, and may be readily removed at the end of the period.

SUMMARY OF THE INVENTION

It is an object of the present invention to provide a vascular filter device and catheter system that enable the vascular filter to be readily implanted and removed.

It is a further object of the present invention to provide vascular filter device that may be readily implanted within a vessel, remain in place for an extended period, and may be readily removed at the end of the period.

These and other objects are achieved by providing a filter device comprising a filter portion attached to a removable vascular stent portion. In a preferred embodiment, the filter portion is a nylon mesh bag or sack, and the removable vascular stent portion comprises a coiled-sheet stent. When the coiled-sheet stent portion is released within a vessel, it uncoils to engage a wall of the vessel and deploys the filter element across the flow path. The nylon mesh sack filters blood passing through the device, catching clots and plaque fragments that might otherwise cause harm.

In accordance with the principles of the present invention, the coiled-sheet stent portion includes a magnetic band disposed along its interior edge that is used to engage and remove the filter device from the vessel. A catheter system comprising an outer sleeve enclosing a shaft having an electromagnetic plate is positioned within the interior of the coiled-sheet stent portion. When the catheter system is disposed adjacent to the magnetic band on the coiled-sheet stent portion, the electromagnetic plate is activated, and the magnetic band is drawn through a slot in the outer sleeve and engages the electromagnetic plate. The shaft holding the electromagnetic plate is then rotated, coiling the stent around the shaft, and capturing the stent within the outer sleeve. As the stent is coiled, the diameter of the nylon mesh sack decreases, thereby enabling the sack and its contents to be readily removed from the vessel.

BRIEF DESCRIPTION OF THE DRAWINGS

Further features of the invention, its nature and various advantages will be more apparent from the accompanying drawings and the following detailed description of the preferred embodiment, in which like reference characters refer to like parts throughout, and in which:

FIGS. 4A and 4B are respectively, a perspective view and cross-sectional view, taken along view line 4B—4B, of the vascular filter device of FIGS. 1 engaged with the catheter system of FIG. 3;

FIGS. 5A and 5B are respectively, a perspective view and cross-sectional view, taken along view line 5B—5B, of the vascular filter device of FIGS. 1 wound within the catheter system of FIG. 3; and FIGS. 6A–6C are cross-sectional views showing reduction of the circumference of the filter sack portion of the filter device of FIGS. 1 during the coiling process of FIGS. 5.

DETAILED DESCRIPTION OF THE INVENTION

Figure 1A:
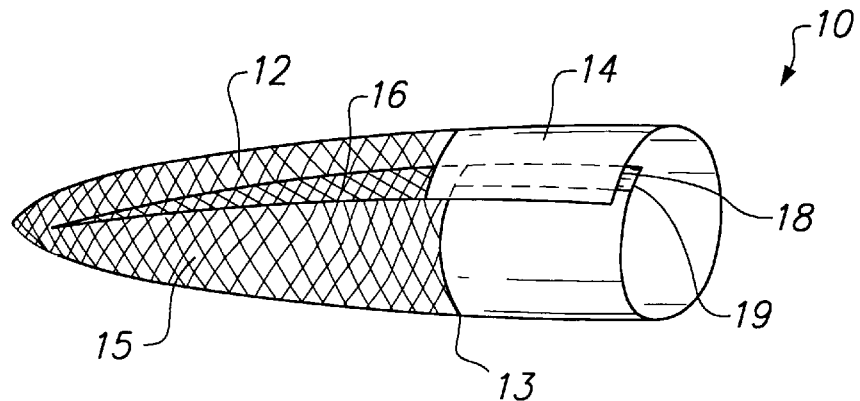
FIGS. 1A and 1B are, respectively, a perspective view of an illustrative filter device constructed in accordance with the present invention in an expanded, deployed state, and in a contracted state for transluminal delivery.
Figure 1B:
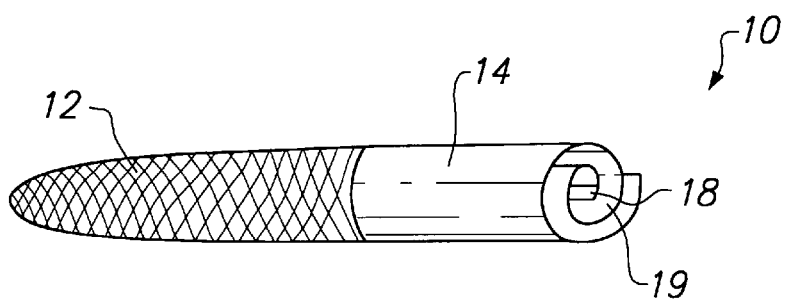

Referring to FIGS. 1A and 1B, illustrative removable vascular filter device 10 constructed in accordance with the present invention is described. Filter device 10 comprises filter sack 12 connected to end 13 of coiled-sheet stent portion 14. Filter sack 12 may be attached to coiled-sheet stent portion 14 by suitable means, such as sutures or a biocompatible adhesive.

Filter sack 12 preferably comprises a monofilament nylon mesh having openings 15 large enough to permit blood to pass freely through the mesh, but sufficiently small to filter out blood clots or plaque fragments that may cause an embolism. For example, for filter applications in vessels such as the superior vena cava or inferior vena cava, openings 15 in sack 12 preferably are between 4 and 9 square millimeters in area. Filter sack 12 also includes fold 16. Fold 16 enhances the ability of the filter sack to fold over itself when coiled-sheet portion 14 is coiled to its delivery state, and during removal of the filter device.

Coiled-sheet stent portion 14 has a contracted delivery state, wherein the stent may be wound down to a small diameter for transluminal delivery, and an expanded, deployed state, wherein the stent engages a wall of a vessel and deploys the filter sack to span the flow area of the vessel. In the deployed state, coiled-sheet stent portion 14 retains filter device 10 at a desired location within a vessel. An example of a coiled-sheet stent suitable for use in vascular filter device 10 of the present invention is described in U.S. Pat. No. 5,433,500 to Sigwart, which is incorporated herein by reference.

Coiled-sheet stent portion 14 preferably comprises a flexible biocompatible metallic material, such as stainless steel or a nickel-titanium alloy. If a nickel-titanium alloy is employed, coiled-sheet stent portion 14 may exhibit either thermally-activated shape memory or pseudoelastic behavior. Coiled-sheet stent portion 14 preferably includes a plurality of apertures in its lateral surface, to enable blood to nourish the vessel endothelium when the stent is implanted in a vessel.

In accordance with one aspect of the present invention, coiled-sheet stent portion 14 includes magnetic band 18 comprising a biocompatible ferrous material disposed along interior edge 19 of coiled-sheet stent portion 14. Magnetic band 18 is used to wind coiled-sheet stent portion 14 within a catheter to retrieve the filter device 10 after implantation in a vessel, as described in detail hereinafter.

With respect to FIG. 1B, filter device 10 is shown in its contracted delivery state, wherein coiled-sheet stent portion 14 is wound to form a series of overlapping turns and has a diameter sufficiently small to enable transluminal delivery. When coiled-sheet stent portion 14 is wound to its contracted delivery state, filter sack 12 also assumes a coiled shape having a reduced diameter. This reduced diameter enables filter device 10 to be readily moved through the vascular system for deployment or removal.

Figure 2A:
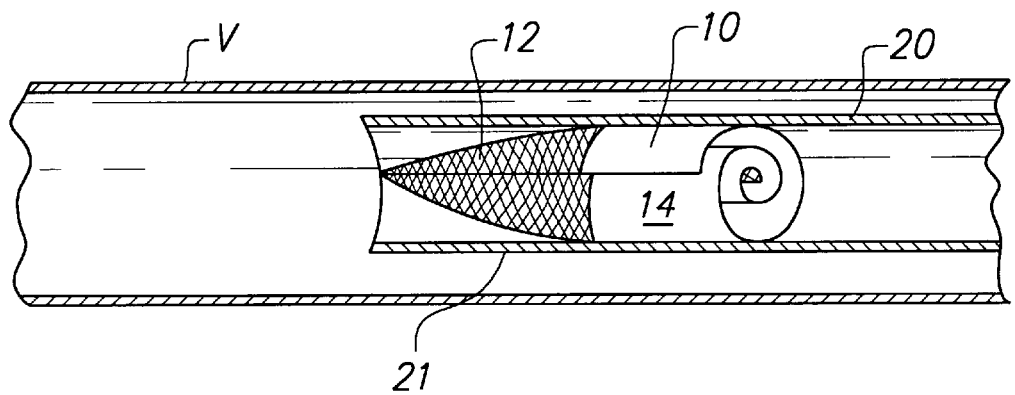
FIGS. 2A–2C illustrate steps of a method of deploying the filter device of FIGS. 1 in a vessel.
Figure 2B:
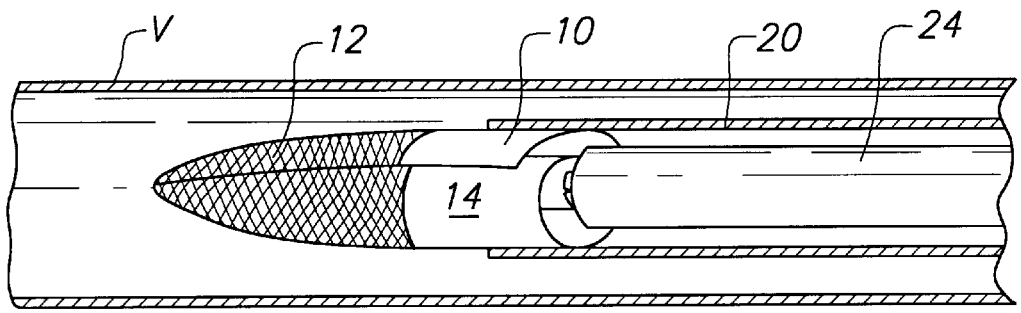
Figure 2C:
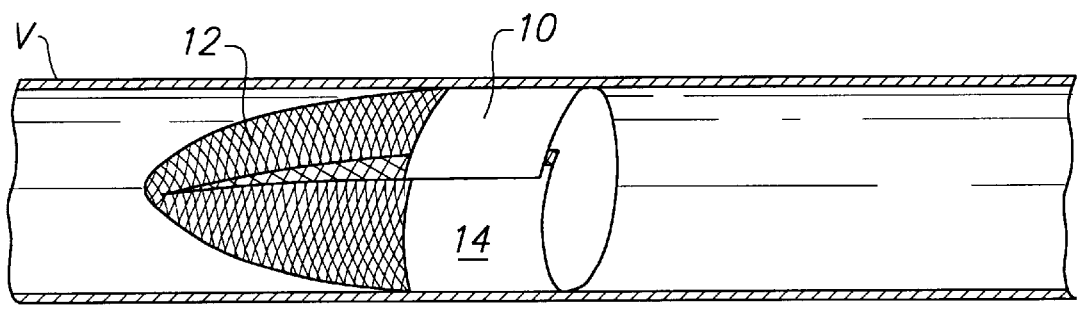

Referring now to FIGS. 2A to 2C, illustrative steps of percutaneously implanting vascular filter device 10 of FIG. 1 are described. As will of course be apparent to one of skill in the art of stent delivery systems, other ways of deploying the stent portion of a filter device constructed in accordance with the present invention may be employed.

In FIG. 2A, catheter 20 includes filter device 10, wound to its contracted delivery state, disposed within distal end 21. Catheter 20 may be percutaneously and transluminally positioned within vessel V, in which the vascular filter device is to be deployed. Alternatively, filter device 10 may be advanced through catheter 20 once catheter 20 is in position.

With respect to FIG. 2B, after catheter 20 is determined to be in a desired position, e.g., using fluoroscopy, pushrod 24 is used to push filter device 10 out of distal end 21 of catheter 20. Alternatively, pushrod 24 may be held stationary while catheter 20 is retracted proximally. In either case, once filter 10 exits distal end 21, coiled-sheet stent portion 14 uncoils (either mechanically or by undergoing a thermal phase transition), and expands into engagement with the circumference of vessel V.

As shown in FIG. 2C, transition of coiled-sheet stent portion 14 to its expanded, deployed diameter also causes filter sack 12 to uncoil and expand across the flow path. Catheter 20 then is withdrawn, leaving filter device 10 in place within vessel V. Filter device 10 may remain in place while procedures such as angioplasty or atherectomy are performed, to capture plaque and blood clots released into the bloodstream by such procedures. Filter device 10 then may be removed using the apparatus of FIG. 3, as described hereinbelow, or left in place for an extended period of time, e.g., several weeks, to filter out any material which may enter the bloodstream later.

Figure 3:
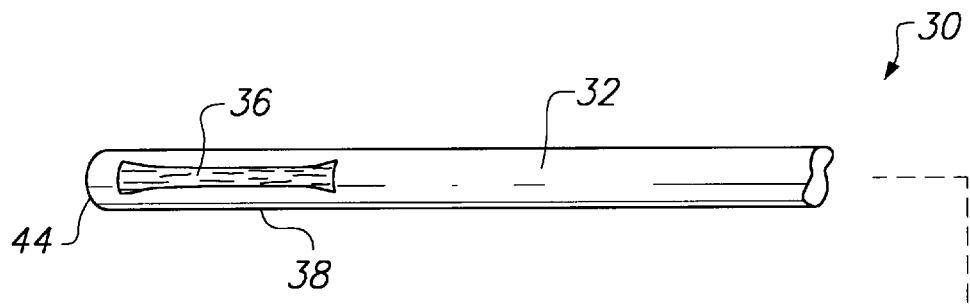
FIG. 3 is an exploded perspective view of an illustrative catheter system constructed in accordance with the present invention.
Figure 3:
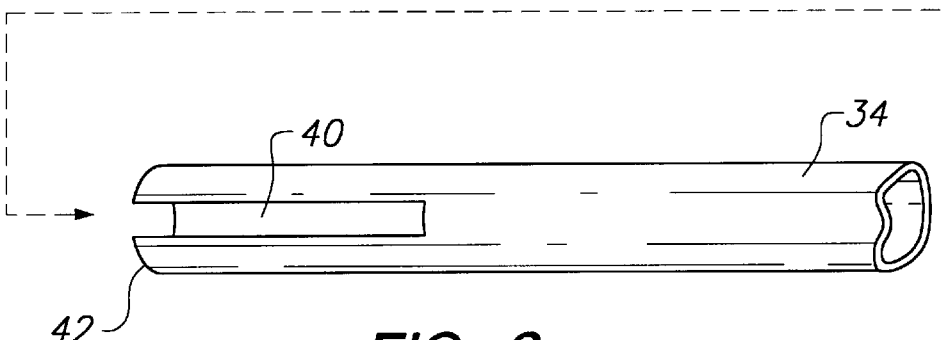

Referring now to FIG. 3, catheter system 30 constructed in accordance with the present invention is described. Catheter system 30, shown in an exploded view in FIG. 3, comprises shaft 32 disposed within outer sleeve 34. Shaft 32 includes electromagnetic plate 36 disposed in distal region 38. Electromagnetic plate 36 is preferably about the same length, or slightly larger than, magnetic band 18 of coiled-sheet stent portion 14 of vascular filter device 10, and may be selectively energized by a power source (not shown), to create a magnetic field surrounding plate 36.

Outer sleeve 34 includes slot 40 extending proximally from distal endface 42 for a distance about equal to the length of electromagnetic plate 36. When assembled, shaft 32 is disposed for rotation within outer sleeve 34 so that distal endface 44 of shaft 32 is approximately flush with distal end 42 of outer sleeve 34, and electromagnetic plate 36 may be aligned with slot 40 of outer sleeve 34. During removal of filter device 10, electromagnetic plate 36 is first activated to engage magnetic band 18, and then shaft 32 is rotated to coil filter device 10 around shaft 32.

Figure 4A:
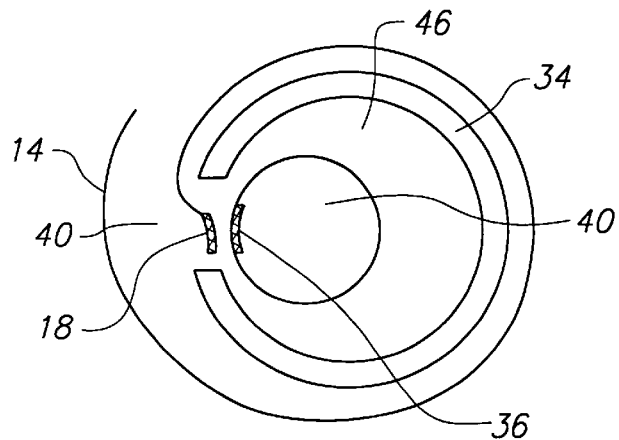
Figure 4A:
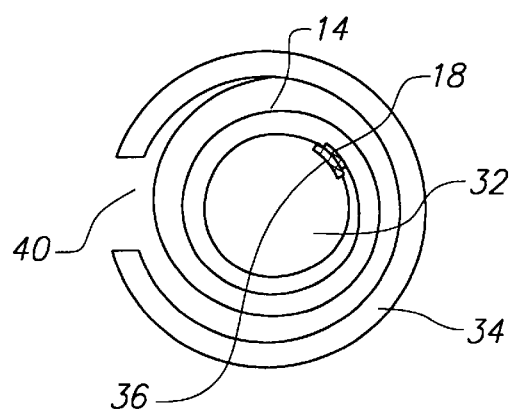
Figure 4A:
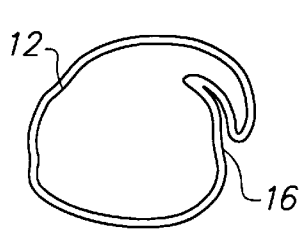
Figure 4A:
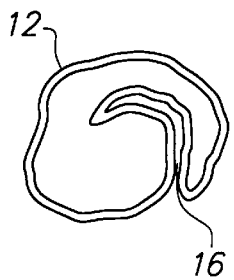
Figure 4A:
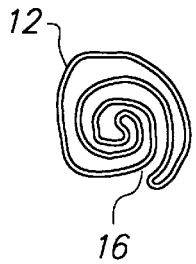
Figure 4A:
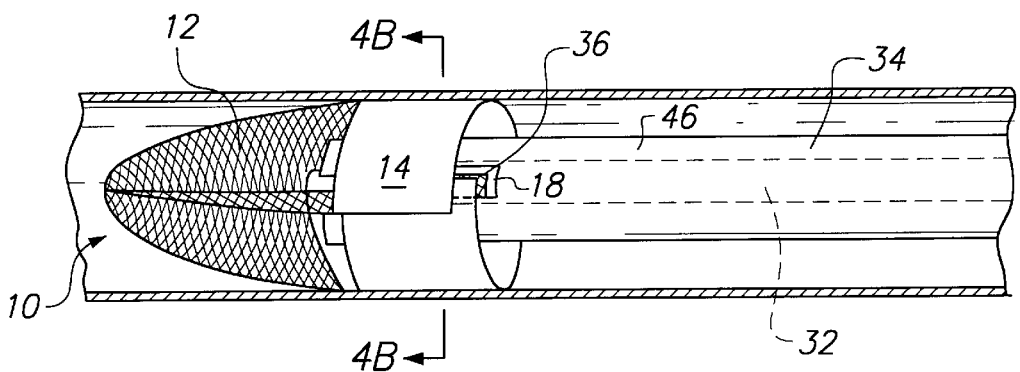

Referring to FIGS. 4A and 4B, catheter system 30 is shown disposed within coiled-sheet stent portion 14 of implanted vascular filter device 10 in preparation for removal of device 10. Electromagnetic plate 36 first is aligned through slot 40 with magnetic band 18 of coiled-sheet stent portion 14, for example, as determined by fluoroscopy. Electromagnetic plate 36 then is activated to create a magnetic field that draws magnetic band 18 through slot 40 and into magnetic engagement with electromagnetic plate 36 (see FIG. 4B). Annular space 46, between outer sleeve 34 and shaft 32, is sized to accommodate coiled-sheet stent portion 14 of filter device 10 when wound around shaft 32.

Figure 5A:
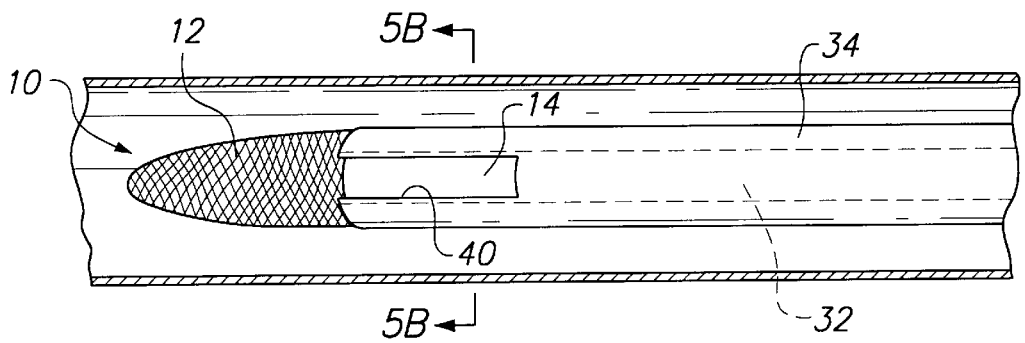

Once magnetic band 18 is engaged with electromagnetic plate 36, shaft 32 is rotated within outer sleeve 34 in a direction that causes coiled-sheet stent portion 14 of device 10 to become wound around shaft 32, as shown in FIGS. 5A and 5B. As coiled-sheet stent portion 14 is wound onto shaft 32, filter sack 12 also is wound to a reduced diameter, as illustrated in FIG. 6A to 6C.

Fold 16 enables filter sack 12 to readily fold over itself, so that it may be wound to a smaller diameter without inhibiting the process of winding coiled-sheet stent portion 14 within outer sleeve 34. Once coiled-sheet portion 14 is coiled to a reduced diameter removal state within outer sleeve 34, catheter system 30, vascular filter device 10, and the contents of filter sack 12 may be transluminally withdrawn.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. A vascular filter comprising:
   a coiled-sheet stent portion having a deployed state, wherein the coiled-sheet stent has a first diameter, and a delivery state, wherein the coiled-sheet stent has a second diameter, smaller than the first diameter; and
   a filter sack attached to an end of the coiled-sheet stent, the filter sack configured to span a flow area of a vessel when the coiled-sheet stent portion transitions to the deployed state.

2. The vascular filter of claim 1, wherein the filter sack further comprises a folded portion that enables the filter sack to be coiled to a diameter smaller than the first diameter.

3. The vascular filter of claim 1, wherein the filter sack comprises a nylon mesh.

4. The vascular filter of claim 3, wherein the filter sack has a multiplicity of openings, each one of the multiplicity of openings having an area between 4 and 9 square millimeters.

5. The vascular filter of claim 1, wherein the coiled-sheet stent portion has an interior edge, the vascular filter further comprising a magnetic band disposed adjacent the interior edge.

6. The vascular filter of claim 1, wherein the coiled-sheet stent portion comprises a flexible biocompatible material.

7. The vascular filter of claim 6, wherein the flexible biocompatible material is selected from a group consisting of stainless steel and a nickel-titanium alloy.

8. The vascular filter of claim 1, wherein the magnetic band comprises a biocompatible ferrous material.

9. The vascular filter of claim 7, wherein the coiled-sheet stent portion self-expands from the delivery state to the deployed state when the vascular filter is released from a restraint.

10. The vascular filter of claim 7, wherein the coiled-sheet stent portion expands from the delivery state to the deployed state when the vascular filter undergoes a thermally-activated transition.

11. Apparatus for removing a vascular filter device, the vascular filter device including a coiled-sheet stent portion and a magnetic band disposed adjacent an interior edge of the coiled-sheet stent portion, the apparatus comprising:
   an outer sleeve having a proximal end, a distal end, a lumen extending between the proximal end and the distal end, and a slot on a lateral surface of the distal end that communicates with the lumen;
   a shaft disposed for rotation within the lumen, the shaft having a proximal and a distal end; and
   an electromagnetic plate disposed on a lateral surface of the shaft near the distal end of the shaft, the electromagnetic plate being selectively switchable between an energized and a non-energized state.

12. The apparatus of claim 11, wherein the electromagnetic plate has a length approximately equal to the length of the magnetic band.

13. The apparatus of claim 12, wherein the slot is configured to expose the electromagnetic plate when the slot and the electromagnetic plate are aligned.

14. The apparatus of claim 11, wherein the slot is configured to permit the magnetic band to pass through the slot.

15. The apparatus of claim 12, wherein an exterior surface of the shaft and an interior surface of the lumen define an annulus sized to accommodate the coiled-sheet stent portion when the coiled-sheet stent portion is wound on the shaft.

16. A method of removing a vascular filter, the vascular filter including a coiled-sheet stent portion, a filter sack connected to an end of the coiled-sheet stent portion, and a magnetic band disposed adjacent an interior edge of the coiled-sheet stent portion, the method comprising:
   providing a shaft having a proximal end, a distal end, and an electromagnetic plate disposed on a lateral surface near the distal end, the electromagnetic plate being selectively switchable between an energized state and a non-energized state;
   positioning the electromagnetic plate near the magnetic band;
   switching the electromagnetic plate to the energized state to cause the magnetic band to engage the electromagnetic plate;
   rotating the shaft to wind the coiled-sheet stent portion around the shaft; and
   withdrawing the shaft and the vascular filter.

17. The method of claim 16, wherein positioning the electromagnetic plate near the magnetic band comprises:
   providing a outer sleeve having a proximal end, a distal end, a lumen extending between the proximal end and the distal end, and a slot in a lateral surface of the outer sleeve at the distal end;
   positioning the outer sleeve so that the slot is in close proximity to the magnetic band; and
   rotating the shaft to align the electromagnetic plate with the slot.

18. The method of claim 17, wherein switching the electromagnetic plate to the energized state further comprises energizing the electromagnetic plate to draw the magnetic band through the slot to engage the electromagnetic plate.

19. The method of claim 18, wherein rotating the shaft includes drawing the coiled-sheet stent portion through the slot so that the coiled-sheet stent portion is wound within the outer sleeve.

20. The method of claim 19, wherein rotating the shaft further comprises winding the filter sack to a reduced circumference.

* * * * *